(12) United States Patent
Bacheldor

(10) Patent No.: US 6,726,646 B2
(45) Date of Patent: Apr. 27, 2004

(54) BRACE CUSHION

(76) Inventor: Neil R. Bacheldor, 26 Kimball Corner Rd., Sebago, ME (US) 04029

( * ) Notice: Subject to any disclaimer, the term of this patent is extended or adjusted under 35 U.S.C. 154(b) by 157 days.

(21) Appl. No.: 10/077,909

(22) Filed: Feb. 20, 2002

(65) Prior Publication Data

US 2002/0138029 A1 Sep. 26, 2002

Related U.S. Application Data

(60) Provisional application No. 60/277,973, filed on Mar. 23, 2001.

(51) Int. Cl.$^7$ .................................................. A61F 5/00
(52) U.S. Cl. ......................................... 602/27; 128/882
(58) Field of Search ................................ 128/845, 869, 128/877, 878, 879, 888, 889; 602/5, 20, 21, 22, 23, 26, 27, 60–65; 2/22

(56) References Cited

U.S. PATENT DOCUMENTS

| | | | | |
|---|---|---|---|---|
| 1,158,208 A | | 10/1915 | Hart | |
| 3,901,225 A | * | 8/1975 | Sconce | 128/DIG. 20 |
| 3,920,006 A | * | 11/1975 | Lapidus | 128/24.1 |
| 4,120,052 A | | 10/1978 | Butler | |
| 4,905,715 A | | 3/1990 | Johnson | |
| 4,949,957 A | * | 8/1990 | Cucchiara | 272/119 |
| 5,031,247 A | | 7/1991 | Carter | |
| 5,393,303 A | * | 2/1995 | Shiono | 602/27 |
| 5,570,470 A | | 11/1996 | Miller | |
| 5,618,263 A | | 4/1997 | Alivizatos | |
| 5,651,375 A | * | 7/1997 | Cunningham | 128/869 |
| 5,674,189 A | | 10/1997 | McDowell et al. | |
| 5,718,669 A | * | 2/1998 | Marble | 602/5 |

* cited by examiner

Primary Examiner—Michael A. Brown
(74) Attorney, Agent, or Firm—Richard C. Litman

(57) ABSTRACT

A padding or cushioning device adapted to be worn with a leg brace includes a cloth body fabricated from soft, supple material. The cloth body is provided with elastic straps so that it may easily be secured to and removed from the leg brace. The cloth body is disposed between the leg and the brace and functions to insulate the skin of the leg from direct contact with the brace, thereby preventing rubbing and/or chafing.

4 Claims, 3 Drawing Sheets

BRACE CUSHION

CROSS-REFERENCE TO RELATED APPLICATION

This application claims the benefit of U.S. Provisional Patent Application Ser. No. 60/277,973, filed Mar. 23, 2001.

BACKGROUND OF THE INVENTION

1. Field of the Invention

The present invention generally relates to devices for protecting the human body. More specifically, the present invention is drawn to a protective cushion adapted to be disposed over a leg brace.

2. Description of Related Art

Unfortunately, there are times when illness or accident-causing injury may require a person to periodically wear a brace of the type that offers support and protection for the lower portion of the leg. Wearing such a leg brace often causes unnecessary discomfort because the brace rubs against the skin, thereby the time that one may wear the brace and conversely, increases the time that the leg is vulnerable to further injury. A device which would efficiently alleviate the discomfort of wearing the brace would certainly be a welcome addition to the art.

There are a plethora of devices in the art designed to protect or cushion human appendages from injury. For example, U.S. Pat. No. 5,031,247 (Carter) and U.S. Pat. No. 5,570,470 (Miller) show protective leg coverings. The coverings are adapted to protect the leg from injuries which might be sustained while operating powered gardening or landscaping equipment.

U.S. Pat. No. 5,674,189 (McDowell et al.) relates to a body shielding device designed to encircle and protect a given area of the body (arm, leg, torso) from exposure to moisture, bacteria and the like.

U.S. Pat. No. 1,158,208 (Hart) and U.S. Pat. No. 4,120,052 (Butler) show cushioned protectors for aiding in preventing injury to a wearer who may participate in various types of sporting activities.

U.S. Pat. No. 5,618,263 (Alivizatos) relates to a soft splint structure which can be wrapped around a jointed limb.

U.S. Pat. No. 4,905,715 (Johnson) discloses a protective padding for the prevention of inner leg skin irritation.

None of the above inventions and patents, taken either singly or in combination, is seen to disclose a cushion adapted to be worn with a leg brace as will be subsequently described and claimed in the instant invention.

SUMMARY OF THE INVENTION

The present invention, to be dubbed "The Roby" (Rashes Omitted By Yourself), comprises a cloth body which can be employed in conjunction with a leg brace. The cloth body is disposed between the leg and the brace and functions to insulate the skin of the leg from direct contact with the brace. Thus positioned, the body will prevent the brace from rubbing the skin and causing the skin to chafe and/or develop a rash. The body is fabricated from soft, supple material and is designed to fit easily over the brace and conform comfortably with the contours of the brace and the leg without producing the cumbersome bulk of other padding devices. Elastic means are provided to securely hold the body to the brace. The cloth body can be removed for washing when necessary.

Accordingly, it is a principal object of the invention to provide a protective, cushioning device for an appendage of the human body.

It is another object of the invention to provide a protective, cushioning device, which device is adapted to be utilized in conjunction with a leg brace.

It is a further object of the invention to provide a protective, cushioning device, which device can be easily secured to and removed from a leg brace.

Still another object of the invention is to provide a protective, cushioning device, which device is fabricated from a soft, supple material.

It is an object of the invention to provide improved elements and arrangements thereof in a protective, cushioning device for the purposes described which are inexpensive, dependable and fully effective in accomplishing their intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
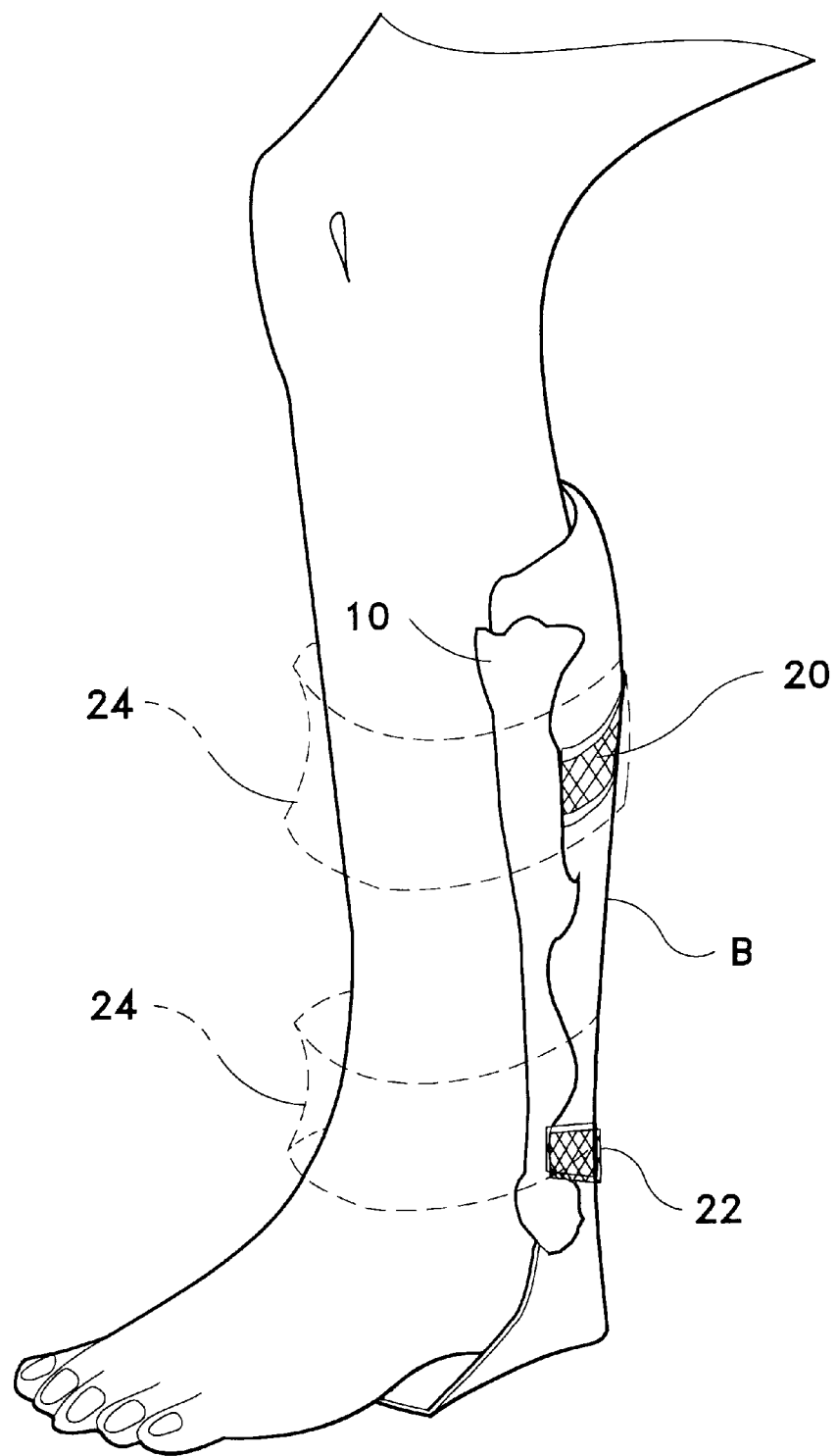
FIG. 1 is an environmental, perspective view of a protective, cushioning device according to the present invention.
Figure 2:
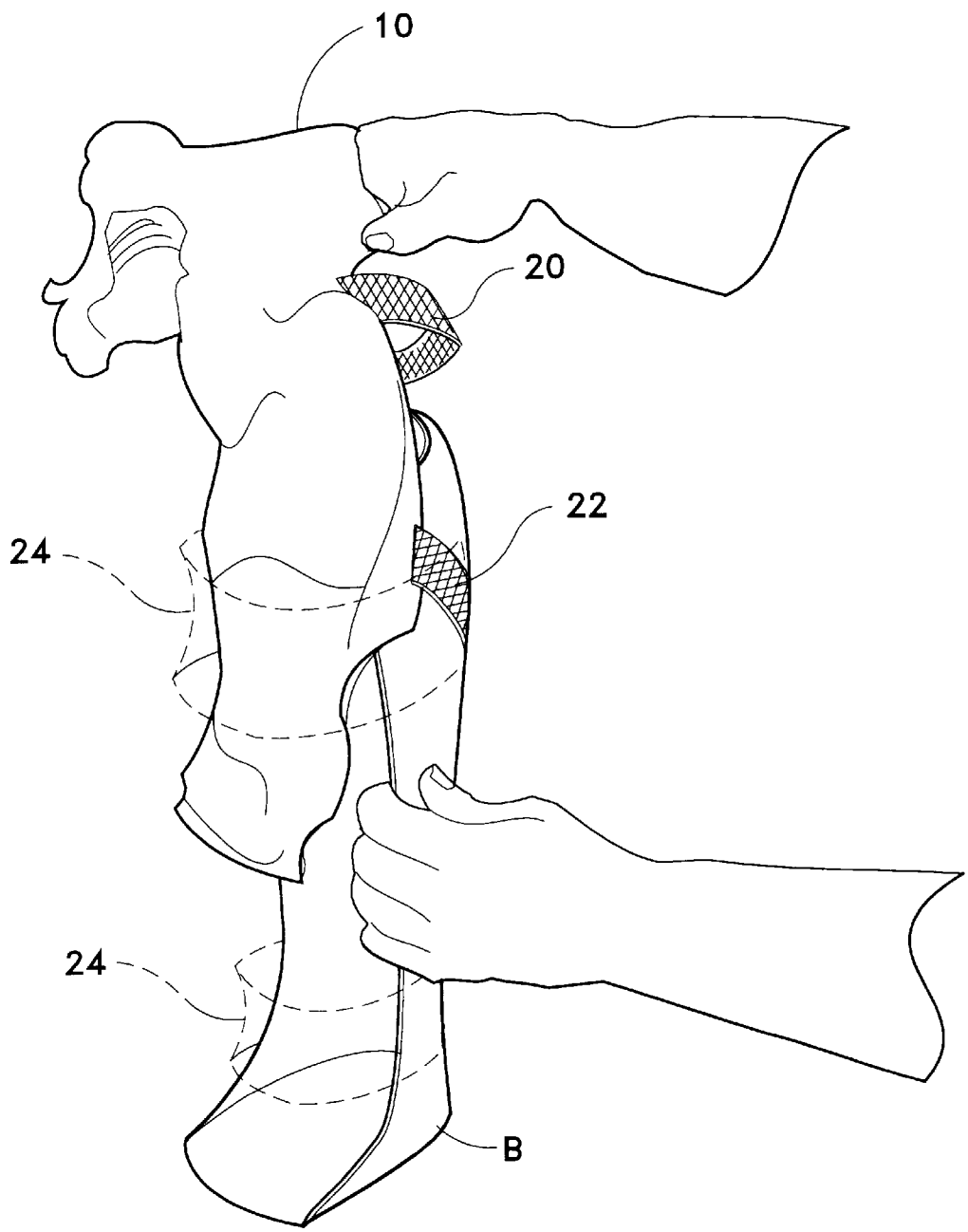
FIG. 2 is a perspective view of a protective, cushioning device according to the present invention.
Figure 3:
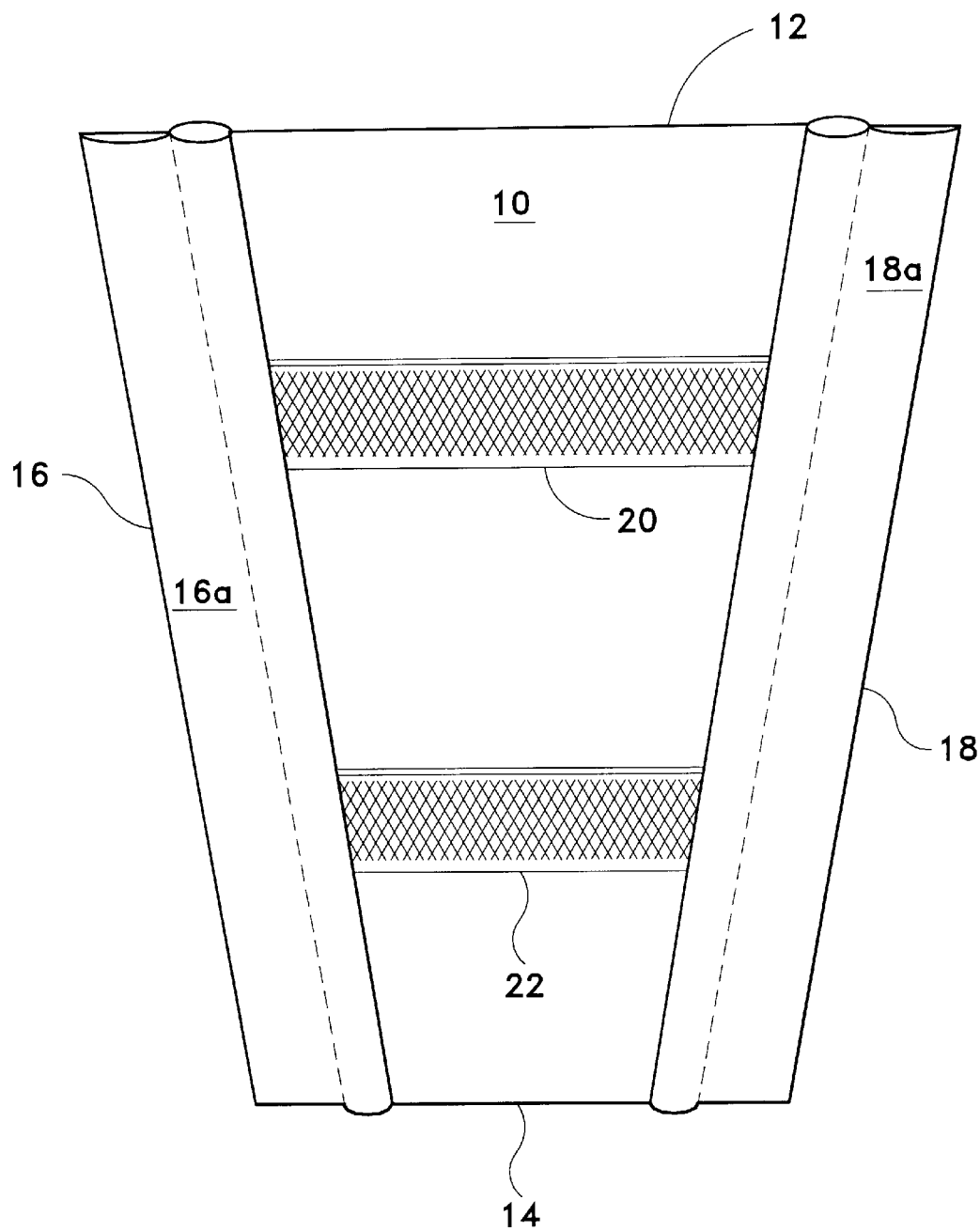
FIG. 3 is a plan view of a protective, cushioning device according to the present invention.

As illustrated in FIGS. 1–3, the present invention comprises a protective body 10 fabricated from soft, supple material such as that used to make sweat-shirts. As best seen in FIG. 3, when laid out, body 10 is configured as a trapezoid. To accommodate the average brace, body 10 will have a height of approximately eighteen inches. The width of the long side 12 will be approximately ten inches and the width of the short side 14 approximately six inches. These dimensions may be altered for special situations if necessary. Angled sides 16, 18 are designed with fold portions 16a, 18a, having inner and outer edges. The fold portions are adapted to drape over the edges of brace B (FIG. 1). Elastic retainer straps 20, 22 extend across body 10 parallel with sides 12 and 14. Elastic straps 20, 22 are attached to body 10 at the inner edges of the fold portion.

Employment of the cushioning device merely requires that the user slip elastic straps 20, 22 over the brace B (FIG. 2) and position the body 10 along the inner surface of the brace in a manner that allows fold portions 16a, 18a to drape over the edges of the brace. The brace may then be attached to the leg in the usual manner such as straps 24 (shown in phantom lines). This quick and easy manipulation will allow the user to wear the brace for extended periods without experiencing rubbing and/or chafing.

It is to be understood that the present invention is not limited to the sole embodiment described above, but encompasses an and all embodiments within the scope of the following claims.

I claim:

1. A cushioning device adapted to be worn with a leg brace, said cushioning device comprising:

a body member fabricated from a soft supple material, said body member configured as a trapezoid having a height, two angled sides, a short side and a long side;

first and second fold portions incorporated respectively into each said two angled sides, each fold portion having an inner edge and an outer edge; and plural elastic straps having longitudinal axes for securing said body member to the leg brace, each elastic strap having a first end attached to the inner edge said first fold portion and a second end attached at the inner edge of said second fold portion.

2. A cushioning device as recited in claim 1, wherein said longitudinal axes of said elastic straps are parallel with said short side and said long side of said body member.

3. A cushioning device adapted to be worn with a leg brace, said cushioning device comprising:

a body member fabricated from a soft supple material, said body member configured as a trapezoid having two angled sides, a height of approximately eighteen inches, a short side of approximately six inches and a long side
of approximately ten inches;

first and second fold portions incorporated respectively into each said two angled sides, each fold portion having an inner edge and an outer edge; and plural elastic straps having longitudinal axes for securing said body member to the leg brace, each elastic strap having a first end attached to the inner edge said first fold portion and a second end attached at the inner edge of said second fold portion.

4. A cushioning device as recited in claim 3, wherein said longitudinal axes of said elastic straps are parallel with said short side and said long side of said body member.

* * * * *